(12) United States Patent
Bohsung et al.

(10) Patent No.: US 9,370,671 B2
(45) Date of Patent: Jun. 21, 2016

(54) METHOD AND DEVICE FOR DETERMINING AN IRRADIATION PLAN FOR A PARTICLE IRRADIATION UNIT

(71) Applicant: SIEMENS AKTIENGESELLSCHAFT, München (DE)

(72) Inventors: Jörg Bohsung, Heidelberg (DE); Thilo Elsässer, Buckenhof (DE); Sven Oliver Grözinger, Hausen (DE); Johann Kim, Erlangen (DE); Robert Neuhauser, Neufahrn (DE); Eike Rietzel, Weiterstadt (DE); Bernd Schweizer, Ketsch (DE); Oliver Thilmann, Augsburg (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/414,608

(22) PCT Filed: Jun. 11, 2013

(86) PCT No.: PCT/EP2013/061956
§ 371 (c)(1),
(2) Date: Jan. 13, 2015

(87) PCT Pub. No.: WO2014/009076
PCT Pub. Date: Jan. 16, 2014

(65) Prior Publication Data
US 2015/0217135 A1 Aug. 6, 2015

(30) Foreign Application Priority Data
Jul. 13, 2012 (DE) .......................... 10 2012 212 340

(51) Int. Cl.
*A61N 5/10* (2006.01)

(52) U.S. Cl.
CPC .............. *A61N 5/103* (2013.01); *A61N 5/1031* (2013.01); *A61N 2005/1087* (2013.01)

(58) Field of Classification Search
USPC ............... 250/492.1, 492.21, 492.22, 492.23, 250/492.3, 526; 378/16, 64, 65; 600/1, 2, 600/411
See application file for complete search history.

(56) References Cited

U.S. PATENT DOCUMENTS

| | | | |
|---|---|---|---|
| 8,217,373 B2 * | 7/2012 | Bert ....................... | A61N 5/103 250/252.1 |
| 8,530,864 B2 * | 9/2013 | Fieres .................. | A61N 5/1031 250/492.1 |

(Continued)

FOREIGN PATENT DOCUMENTS

| | | |
|---|---|---|
| DE | 102008009765 A1 | 9/2009 |
| DE | 102009033297 A1 | 1/2011 |

(Continued)

OTHER PUBLICATIONS

German Office action for related German Application No. 10 2012 212 340.7, dated Apr. 6, 2013, with English Translation.

(Continued)

*Primary Examiner* — Bernard Souw

(74) *Attorney, Agent, or Firm* — Lempia Summerfield Katz LLC

(57) ABSTRACT

An irradiation plan for a particle irradiation unit is determined in a first run based on a specified target volume in a test object and a specified dose distribution to apply the particle beam in the target volume. The target volume includes a plurality of isoenergy layers. The irradiation plan may be determined in a second run with an additional condition that at least one of the isoenergy layers, determined according to one or more criteria, is not irradiated. Alternatively, the irradiation plan may be determined in a second run with an additional condition that only certain isoenergy layers, determined according to one or more criteria, are irradiated.

20 Claims, 4 Drawing Sheets

(56) References Cited

U.S. PATENT DOCUMENTS

| | | | |
|---|---|---|---|
| 8,598,546 B2 * | 12/2013 | Bert | A61N 5/10 250/492.1 |
| 8,809,814 B2 * | 8/2014 | Bert | A61N 5/103 250/492.3 |
| 2010/0074408 A1 * | 3/2010 | Bert | A61N 5/103 378/65 |
| 2010/0327188 A1 | 12/2010 | Bert et al. | |
| 2011/0065974 A1 * | 3/2011 | Rietzel | A61N 5/103 600/1 |
| 2012/0187314 A1 | 7/2012 | Bert et al. | |
| 2013/0150647 A1 | 6/2013 | Chen et al. | |
| 2015/0196781 A1 * | 7/2015 | Bohsung | A61N 5/1031 600/1 |

FOREIGN PATENT DOCUMENTS

| | | |
|---|---|---|
| DE | 102011088160 B3 | 5/2013 |
| EP | 2392383 A1 | 12/2011 |
| EP | 2510978 A1 | 10/2012 |

OTHER PUBLICATIONS

Kanematsu N. et al, "Treatment planning for the Layer-stacking irradiation system for three-dimensional conformal heavy-ion radiotherapy," Med. Phys., vol. 12, No. 12, pp. 2823-2829, 2002.

PCT International Search Report and Written Opinion of the International Searching Authority dated Sep. 26, 2013 for corresponding PCT/EP2013/061956.

* cited by examiner

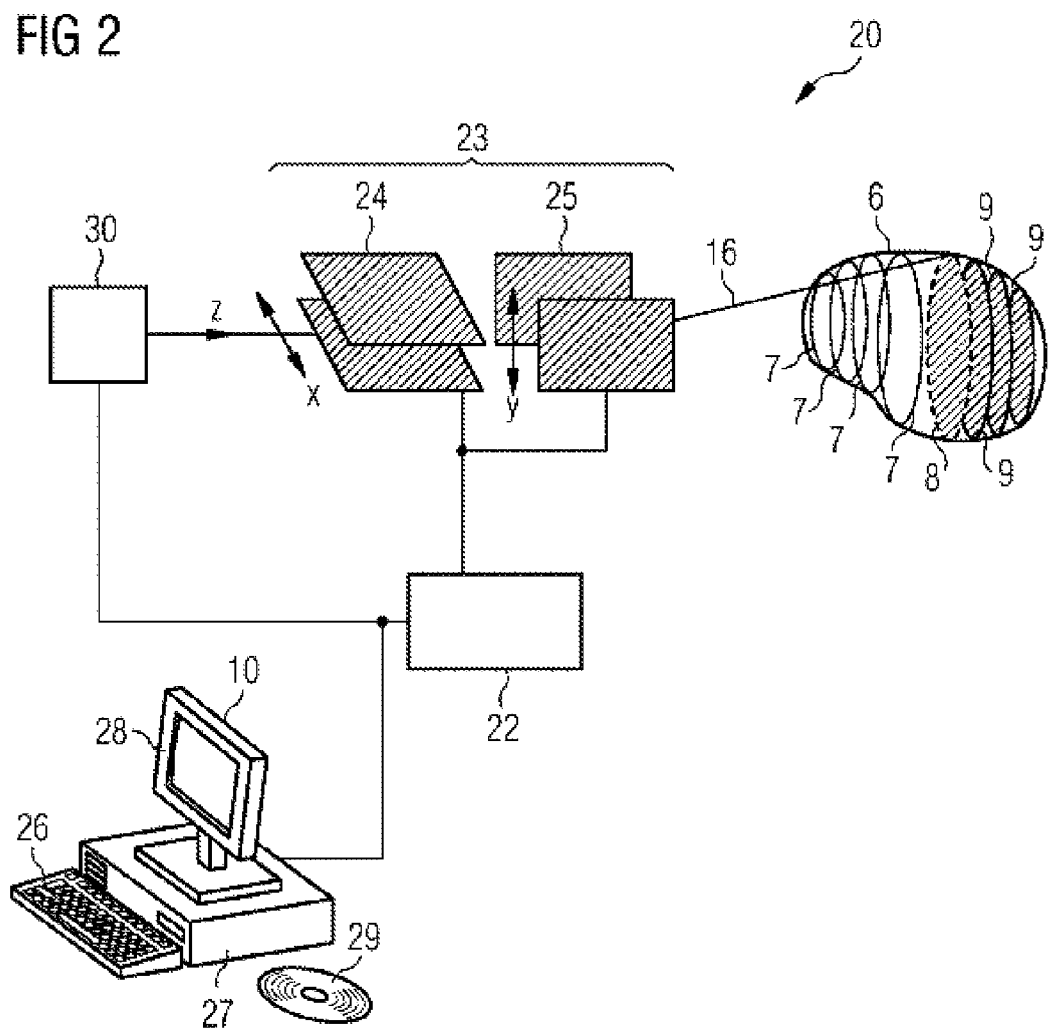

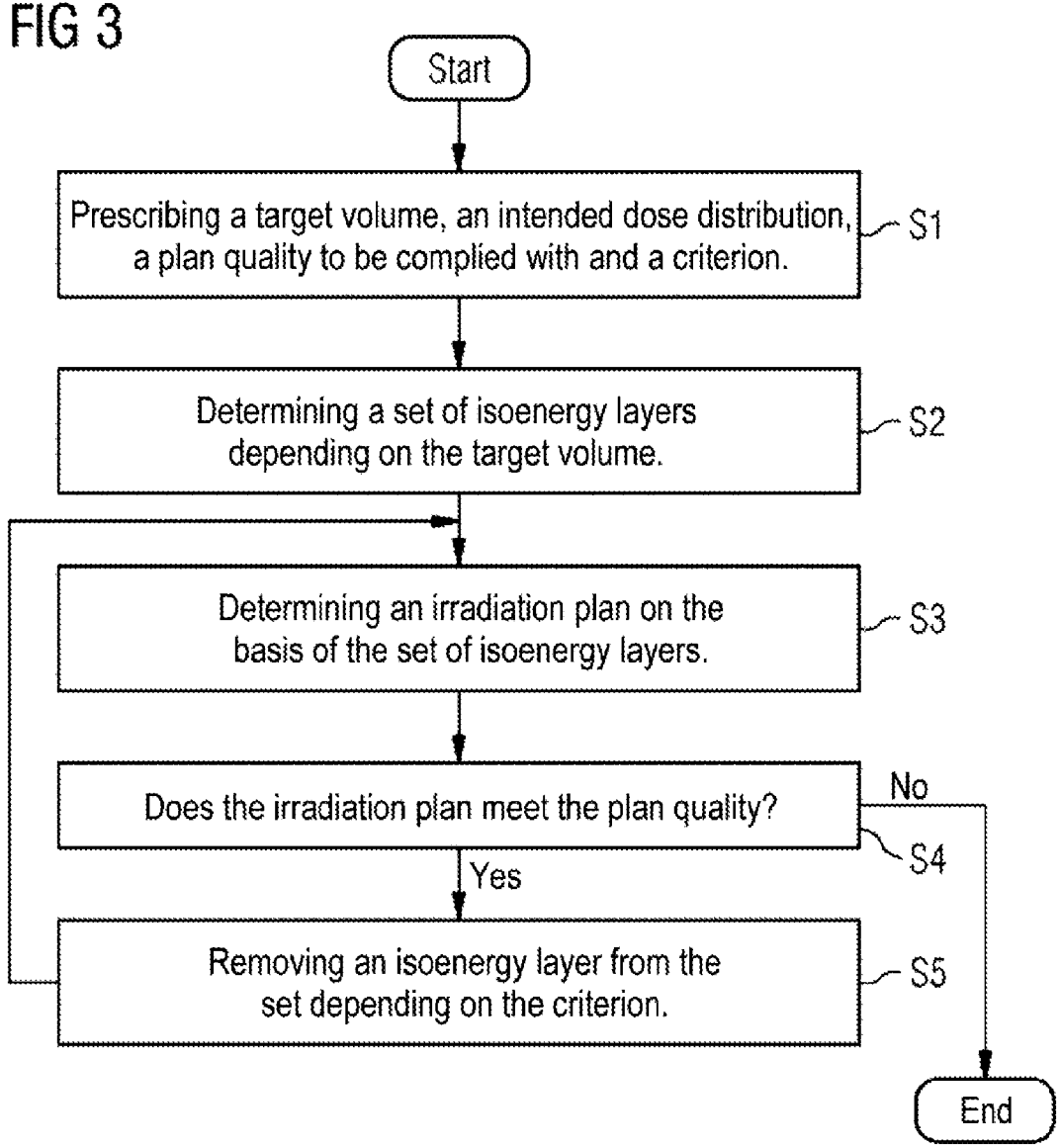

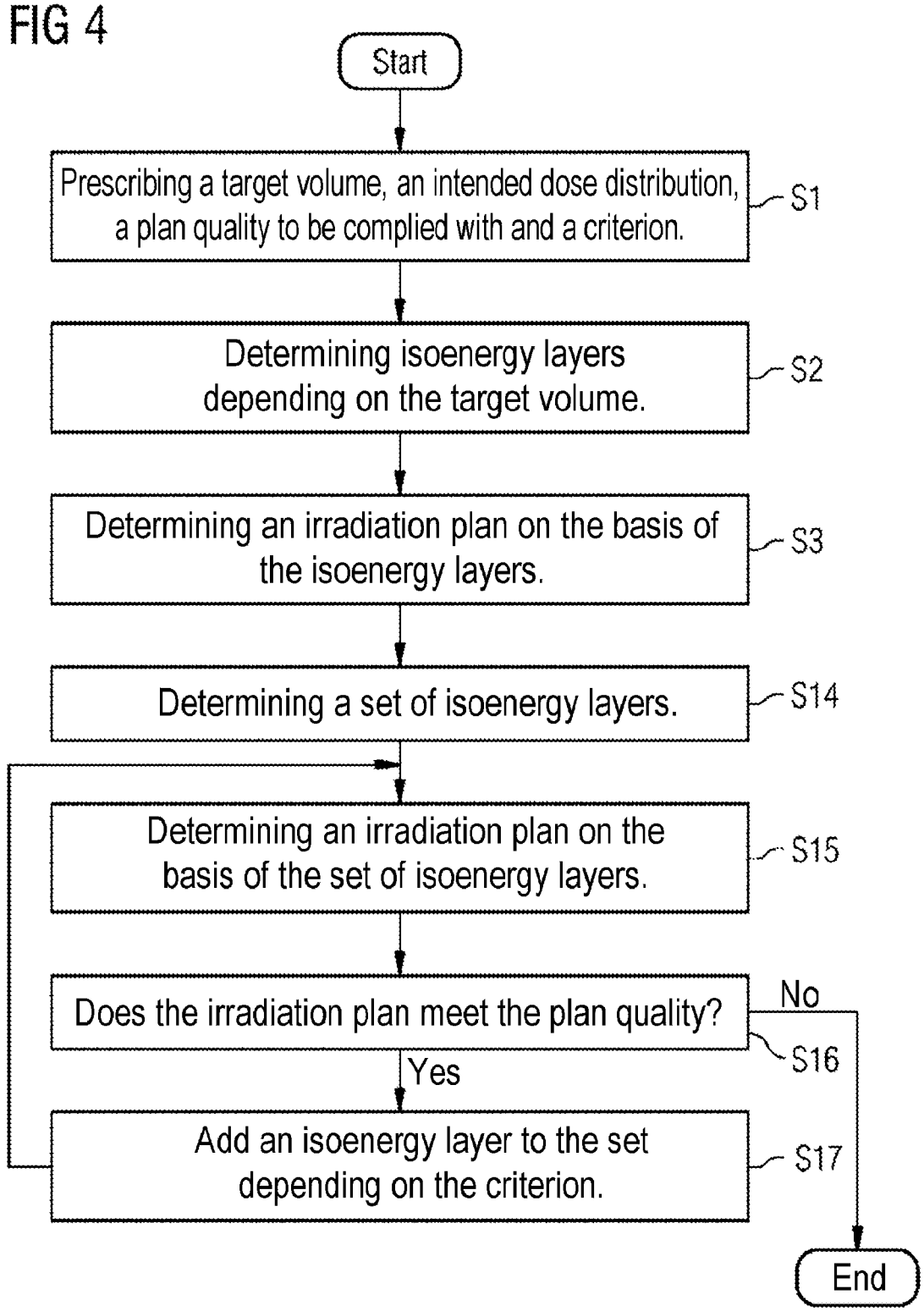

METHOD AND DEVICE FOR DETERMINING AN IRRADIATION PLAN FOR A PARTICLE IRRADIATION UNIT

RELATED APPLICATIONS

This application is the National Stage of International Application No. PCT/EP2013/061956, filed Jun. 11, 2013, which claims the benefit of German Patent Application No. DE 102012212340.7, filed Jul. 13, 2012. The entire contents of both documents are hereby incorporated herein by reference.

TECHNICAL FIELD

The present teachings relate generally to methods and devices for determining an irradiation plan for a particle irradiation unit and, in some embodiments, to a particle irradiation unit.

BACKGROUND

In therapy planning for particle radiotherapy, an irradiation plan that defines control parameters for irradiating an examination object may be created in advance. The irradiation plan is used to plan the irradiation of an object in accordance with specific prescriptions (e.g., target volume or dose distribution).

Particle radiotherapy is a well-established method that may be used to irradiate tissue afflicted by tumor diseases. In particle radiotherapy, charged particles (e.g., protons, carbon ions, or other ions) are accelerated to high energies, shaped to make a particle beam, and conveyed via a high-energy transportation system to one or more irradiation rooms. The target volume of the treatment object is irradiated by the particle beam in an irradiation room. Tissue outside of the target volume may be irradiated as well.

If accelerators with an active energy variation are used in particle radiotherapy, particle beams with different energies are used for irradiating the target volume. As a result, isoenergy layers form that may lie in and outside of the target volume. In an isoenergy layer, the particle beam applies particles with the same energy, such that the particles of the particle beam to be positioned on the respective isoenergy layer have an energy that differs from the energy of the particles for other isoenergy layers. All particles for an isoenergy layer may be applied with the aid of one spill (e.g., by a single accelerator fill) since loading or generating a new spill takes a number of seconds. In total, the interruption time for generating a new spill takes up about half of the overall irradiation duration depending on the number of particles to be applied. To provide a patient-friendly irradiation of minimum duration, an accurate application of dose in the target volume, and an economical operation of the particle irradiation unit, the direct irradiation time and the overall irradiation duration may be minimized. The quality of the irradiation plan to be assessed by the treating medical practitioner may be considered.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, the present teachings facilitate minimization of overall irradiation duration while maintaining an acceptable plan quality when determining an irradiation plan for a particle irradiation unit.

In accordance with the present teachings, a first method for determining (e.g., automatically) an irradiation plan for a particle irradiation unit is provided. With the aid of the particle irradiation unit, a target volume in an examination object is irradiated by a particle beam in accordance with the irradiation plan. Starting from a prescribed target volume and a predetermined dose distribution (e.g., intended dose distribution) in the target volume, the irradiation plan is determined in a first pass to deposit or apply the dose of the particle beam into or to the target volume. The target volume includes a plurality of isoenergy layers of high quality (e.g., closely matched to the intended dose distribution) based on the irradiation plan. The irradiation plan is determined in a second pass, such that one or more isoenergy layers are not taken into account and, therefore, are not irradiated. The dose for other isoenergy layers may be changed to compensate for the dose gaps created by not taking into account at least one isoenergy layer. The isoenergy layer or the plurality of isoenergy layers (e.g., referred to as n isoenergy layers below) may be determined based on one or more of the following criteria:

$1^{st}$ Criterion:

The n isoenergy layers with the lowest energy are not taken into account and, therefore, are not irradiated. In other words, the n isoenergy layers wherein the particle beam for irradiation of the layers has an energy below a minimum peak energy are not irradiated.

The minimum peak energy may be defined in absolute terms (e.g., without taking into account the respective energies of the isoenergy layers) or relative terms (e.g., taking into account the respective energies of the isoenergy layers). By way of example, if the three (n) isoenergy layers with the lowest energies are not to be taken into account or irradiated, the minimum peak energy is defined relative to the energy of the isoenergy layer with the third lowest (n lowest) energy. For example, the minimum peak energy lies slightly above the energy of the particles of the isoenergy layer with the third lowest (n lowest) energy. By contrast, an absolute definition of the minimum peak energy does not factor in the respective energies of the isoenergy layers. Thus, all isoenergy layers below a predetermined energy (e.g., 150 MeV) are not irradiated. This criterion is independent of how many of the isoenergy layers, or what percentage of the isoenergy layers, are not irradiated.

$2^{nd}$ Criterion:

The n isoenergy layers with the highest energy are not taken into account and, therefore, are not irradiated. In other words, the n isoenergy layers wherein the particle beam for irradiation of the layers has an energy above a maximum peak energy are not irradiated.

The maximum peak energy may be defined in absolute terms (e.g., without taking into account the respective energies of the isoenergy layers) or relative terms (e.g., taking into account the respective energies of the isoenergy layers). By way of example, if the three (n) isoenergy layers with the highest energies are not to be taken into account or irradiated, the maximum peak energy is defined relative to the energy of the isoenergy layer with the third highest (n highest) energy. The maximum peak energy lies slightly below the energy of the particles of the isoenergy layer with the third highest (n highest) energy. By contrast, an absolute definition of the maximum peak energy does not take into account the respective energies of the isoenergy layers.

3rd Criterion:

The n isoenergy layers that, according to the irradiation plan determined in the first pass, have the smallest number of raster points of the isoenergy layers, are not irradiated. In other words, the raster-point number is determined for each isoenergy layer after the first pass. The n isoenergy layers having the lowest raster-point number in relation to the other isoenergy layers are established. The n isoenergy layers thus established are not taken into account and are not irradiated.

As used herein, the phrase "raster point" refers to a point in a plane through the isocenter that is orthogonal to the particle beam. The particle beam is directed to a raster point that determines the direction of the particle beam.

4th Criterion:

The n isoenergy layers that, according to the irradiation plan determined in the first pass, have the smallest overall number of particles of the isoenergy layers are not irradiated. In other words, the overall particle number for each isoenergy layer is established after the first pass. The n isoenergy layers wherein the overall particle number is lowest in relation to the other isoenergy layers are determined. The n isoenergy layers thus determined are not taken into account and are not irradiated.

5th Criterion:

The n isoenergy layers that, according to the irradiation plan determined in the first pass, make the smallest dose contribution to the overall dose to be applied in the target volume are not irradiated. In other words, the dose to be applied in the target volume by the respective isoenergy layer is determined for each isoenergy layer after the first pass. The n isoenergy layers wherein the dose is lowest in relation to the other isoenergy layers are determined. The n isoenergy layers thus determined are not taken into account and are not irradiated.

6th Criterion:

The n isoenergy layers that, according to the irradiation plan determined in the first pass, make the smallest contribution to a target function that is optimized for determining the irradiation plan are not irradiated. In other words, the contribution to the target function is determined for each isoenergy layer after the first pass. The n isoenergy layers are determined wherein the contribution is smallest in relation to the other isoenergy layers. The n isoenergy layers thus determined are not taken into account and are not irradiated.

7th Criterion:

The n isoenergy layers that, according to the irradiation plan determined in the first pass, have the smallest dose compensation error are not irradiated. In other words, the dose compensation error is determined for each isoenergy layer after the first pass. The n isoenergy layers are determined wherein the dose compensation error in relation to the other isoenergy layers is the lowest. The n isoenergy layers thus determined are not taken into account and are not irradiated.

8th Criterion:

The n isoenergy layers—the omission of which, after a renewed optimization, leads to the smallest change in the target function value—are not irradiated. In other words, the n isoenergy layers wherein the dose-loss associated with the omission thereof may best be compensated for by the other isoenergy layers are not irradiated. A complete optimization of the target function may be performed under the assumption that n isoenergy layers are not irradiated to establish these n isoenergy layers.

In other words, the target function value is respectively generated by an optimization for different sets of n isoenergy layers. An assumption is made that the respective set of n isoenergy layers is not irradiated. From these sets, the set of n isoenergy layers is ultimately selected, wherein the change in the target function value is lowest relative to a target function value generated by an optimization under the assumption that the respective set of n isoenergy layers is also irradiated.

The number n for each criterion is a natural number. Thus, only one isoenergy layer may not be taken into account or not irradiated.

The isoenergy layers that are not to be irradiated according to criteria 1 and 2 may also be determined in a single pass (e.g., as opposed to the first and second pass) since the energy of the particle beam for the respective isoenergy layer is known prior to determining the irradiation plan. Thus, the irradiation plan may be generated during the first pass under an assumption that the n isoenergy layers in accordance with criteria 1 and/or 2 are not irradiated. The number of isoenergy layers to be potentially irradiated may be reduced in the first pass or prior to the first pass (e.g., depending on a tumor size to be irradiated).

The target function is optimized for determining the irradiation plan. Each isoenergy layer supplies a contribution to the target function. The contribution of the respective isoenergy layer may include a sum of positive contributions (e.g., dose contribution to the overall dose) and negative contributions (e.g., time duration of the irradiation, irradiation of healthy tissue). The sign of the contribution of the respective isoenergy layer may be taken into account when establishing the n isoenergy layers with the smallest contribution to the target function.

The target function may include a penalty term or negative contribution. The penalty term becomes larger as the number of irradiated isoenergy layers increases.

If an isoenergy layer or a plurality of isoenergy layers is/are not irradiated, the omitted dose contribution resulting from omission of the isoenergy layer(s) is offset by a corresponding dose increase of the isoenergy layers to be irradiated. To determine the dose compensation error, a first dose distribution may be determined under an assumption that both the isoenergy layers to be irradiated and the isoenergy layers not to be irradiated are irradiated. A second dose distribution is determined under an assumption that only the isoenergy layers to be irradiated are irradiated, such that the isoenergy layers have a correspondingly higher dose for compensating for the non-irradiated isoenergy layers. By way of example, the dose compensation error may correspond to a difference between the first dose distribution and the second dose distribution.

Equation (1) determines the dose difference $r_i(IES)$ present or occurring at any point i ("point of interest") in the target volume.

$$r_i(IES) = d_i - d_i(IES) \quad (1)$$

The dose difference $r_i(IES)$ is calculated from the difference between the planned intended dose $d_i$ for point i, and the intended dose proportion $d_i(IES)$ caused by irradiation of the specific isoenergy layer IES. Using equation (1), a global compensation factor c may be determined. A product of the dose difference $r_i(IES)$ and the compensation factor corresponds to the intended dose $d_i$ applicable for the corresponding point (e.g., at every point i of the target volume).

However, even if the omission of a specific isoenergy layer IES is compensated for by the particle number, determined for each raster point of the isoenergy layers still to be irradiated, and multiplied by the compensation factor c, a minimum error err(IES) (e.g., a "dose compensation error" as used herein) that may be determined in accordance with equation (2), occurs.

$$err(IES) = \min_c \sum_i (c \times r_i(IES) - d_i)^2 \quad (2)$$

Accordingly, the ideal compensation factor $c_{opt}$, wherein the dose compensation error is minimal, is determined to identify the minimum error err(IES) for a specific isoenergy layer IES. The ideal compensation factor $c_{opt}$ may be determined as a result of the condition that the first derivative with respect to c of the dose compensation error function err(IES) according to equation (2) has the value 0. Thus, the ideal compensation factor $c_{opt}$ may be determined by equation (3).

$$c_{opt} = \frac{\sum_i d \times r_i(IES)}{\sum_i (r_i(IES))^2} \quad (3)$$

For the ideal compensation factor $c_{opt}$, the corresponding minimum dose compensation error err(IES) emerges for the corresponding isoenergy layer IES according to equations (4) or (5).

$$err(IES) = \sum_i d_i^2 - \frac{\left(\sum_i d_i \times r_i(IES)\right)^2}{\sum_i (r_i(E))^2} \quad (4)$$

$$err(IES) = \left(1 - \frac{\left(\sum_i d_i \times r_i(IES)\right)^2}{\sum_i d_i^2 \times \sum_i (r_i(E))^2}\right) \times \sum_i d_i^2 \quad (5)$$

To determine the isoenergy layer for which the dose compensation error determined according to equations (2), (4) or (5) is smallest, the dose compensation error according to equations (2), (4) and/or (5) may be determined for each isoenergy layer, and the isoenergy layer may be selected wherein the dose compensation error err(IES) has the smallest value.

Equations (2) through (5) described above assume that there is only one global compensation factor c or $c_{opt}$ that is the same for all isoenergy layers to be irradiated. To compensate for the isoenergy layer IES to be omitted, the particle numbers planned for each raster point for each isoenergy layer to be irradiated are multiplied by the compensation factor.

Alternatively, an individual compensation factor may be determined for each isoenergy layer to be irradiated. As a result, a larger compensation factor may be applied to the isoenergy layers that lie in the vicinity of the isoenergy layer to be omitted.

For an optimal selection of individual compensation factors, the quadratic deviation F from the intended dose $d_i$ may be determined for each relevant point i in the target volume based on equation (6) below.

$$F = \sum_i (k_i - d_i)^2 \quad (6)$$

In equation (6), $k_i$ corresponds to the actual dose at the point i.

To determine which isoenergy layer may best be omitted, the set of individual compensation factors for the isoenergy layers to be irradiated is determined, wherein the quadratic deviation F in equation (6) has the smallest value (e.g., for each isoenergy layer that according to the current irradiation plan is still to be irradiated). The isoenergy layer wherein the quadratic deviation F has the minimum smallest value of all isoenergy layers is now omitted.

In accordance with the present teachings, the omission of an isoenergy layer may be simulated, such that the omission thereof is compensated for by one of the following procedures: (a) the dose of the isoenergy layers to be irradiated is increased by a global compensation value to compensate for the omission of the respective isoenergy layer; (b) an individual compensation factor is determined for each isoenergy layer by a fast optimization, wherein the individual compensation factor increases the dose of the respective isoenergy layer to be irradiated to compensate for the omission of the respective isoenergy layer; and (c) under the assumption that the respective isoenergy layer is omitted, a fictitious irradiation plan is generated based on a complete optimization, such that the actual dose for each isoenergy layer to be irradiated is re-determined.

Thus, in accordance with the present teachings, there are multiple approaches for determining the isoenergy layer the omission of which leads to the smallest quadratic deviation F among all the isoenergy layers. These approaches may differ not only in quality but also in computational complexity.

For embodiments operating with a global compensation factor, alternative embodiments operating with individual compensation factors, and the procedure described above, one or a plurality of isoenergy layers may be removed from irradiation in one act. In each instance, a subset—the omission of which during irradiation leads to, for example, the smallest quadratic deviation F according to equation (6)—is selected from the superset of isoenergy layers to be irradiated according to the current irradiation plan.

To determine the n isoenergy layers that are not to be irradiated in accordance with one or more of the above-described criteria, a ratio may be formed between the number or proportion, in accordance with the respective criterion, of the n isoenergy layers and a sum of the numbers or proportions, in accordance with the respective criterion, of all isoenergy layers. The n isoenergy layers are determined such that the ratio lies just below a predetermined threshold but exceeds the predetermined threshold upon the addition of a further isoenergy layer to the n isoenergy layers.

By way of example, in criterion 3, the ratio may be formed such that the sum of the raster-point numbers of the n isoenergy layers is correlated with the sum of the raster-point numbers of all isoenergy layers. The n isoenergy layers contain the isoenergy layers with the smallest raster-point numbers, such that the ratio lies just below the predetermined threshold (e.g., 30% or 0.3).

With respect to criterion 5, the ratio may be formed such that the sum of the dose contributions of the n isoenergy layers is correlated with the overall dose (e.g., the sum of the dose contributions of all isoenergy layers). The n isoenergy layers contain the isoenergy layers with the smallest dose contributions, such that the ratio lies just below the predetermined threshold (e.g., 0.2).

The n isoenergy layers may also be determined relative to a maximum value. For example, the sum of the numbers (e.g., raster-points numbers or overall numbers of particles) or the proportions of the n isoenergy layers are formed in accordance with the respective criterion. The n isoenergy layers are selected such that the sum lies just below a predetermined maximum value but exceeds the predetermined maximum value upon the addition of one additional isoenergy layer to the set of n isoenergy layers.

By way of example, a maximum sum of the overall numbers of particles may be prescribed in criterion 4. The n isoenergy layers with the lowest overall numbers of particles are determined such that the sum of the overall numbers of particles of the n isoenergy layers lies just below the prescribed maximum sum.

Similarly, a maximum contribution to the target function may be prescribed in criterion 6. The n isoenergy layers with the smallest contributions to the target function are determined such that the sum of the contributions to the target function of the n isoenergy layers lies just below the maximum contribution. In some embodiments, a condition to be complied with by the irradiation plan is prescribed. The set of n isoenergy layers that is not irradiated is now expanded by the addition of further isoenergy layers in accordance with one of the above-described criteria for as long as the irradiation plan continues to comply with the condition. By way of example, an additional isoenergy layer may be added to the n isoenergy layers in an incremental fashion in accordance with one of the above-described criteria until the irradiation plan— which is generated starting from the isoenergy layers to be irradiated (e.g., without the current set of n isoenergy layers)—no longer complies with the prescribed condition. The last-added isoenergy layer is then removed from the set of n isoenergy layers to determine the irradiation plan.

By way of example, the prescribed condition may be compliance with specific tolerance limits of organs at risk, conditions defined by dose/volume histograms, compliance with tolerance limits of the dose distribution in the target volume, correspondence between actual dose distribution and intended dose distribution, and combinations thereof.

In accordance with the present teachings, the irradiation plan may be generated in more than two passes. For example, n isoenergy layers that are not irradiated may be determined according to the respective criterion after each pass (except, perhaps, for the last pass), and taken into account in the next pass for determining the irradiation plan. The additional isoenergy layers that are not to be irradiated are determined after each pass depending on the properties (e.g., raster-point number, overall number of particles) of the isoenergy layers determined by the last-determined irradiation plan.

Thus, the selection of the next isoenergy layer(s) not to be irradiated takes into account the remaining isoenergy layers or the isoenergy layers that are still provided for irradiation. An irradiation plan is determined starting from the isoenergy layers not to be irradiated, and the next isoenergy layers not to be irradiated are then determined based one or more selected criteria. The isoenergy layers not to be irradiated are then added to the set of isoenergy layers not to be irradiated or removed from the set of isoenergy layers to be irradiated.

In some embodiments, the irradiation plan is generated in more than two passes as further described below.

If the irradiation plan is generated in more than two passes, isoenergy layers that are no longer taken into account in the irradiation plan generation (and, therefore, that are not irradiated) are determined according to the respective criteria in each pass. Each pass apart from the first pass is based on the planning result of the preceding pass. Further operations for optimizing the irradiation plan may be undertaken between two passes. For example, the irradiation plan may be re-optimized based on the current isoenergy layers to be irradiated for the respective pass.

In accordance with the present teachings, a further second method for determining an irradiation plan for a particle irradiation unit is also provided. The particle irradiation unit is configured to irradiate a target volume in an examination object with a particle beam depending on the irradiation plan. The target volume and a predetermined dose distribution are prescribed. The irradiation plan is determined in a first pass to apply the particle beam in accordance with the predetermined dose distribution in the target volume. The target volume includes a plurality of isoenergy layers. In a second pass, the irradiation plan is determined with an additional condition that only selected or specific isoenergy layers of the plurality of isoenergy layers are irradiated. The selected or specific isoenergy layers are determined according to at least one of the following criteria:

$1^{st}$ Criterion:

Only the isoenergy layers wherein the particle beam for irradiation thereof has an energy above a minimum peak energy are determined and irradiated.

$2^{nd}$ Criterion:

Only the isoenergy layers wherein the particle beam for irradiation thereof has an energy below a maximum peak energy are determined and irradiated.

$3^{rd}$ Criterion:

Only the isoenergy layers that, according to the irradiation plan determined in the first pass, have the largest number of raster points relative to the other isoenergy layers are determined and irradiated.

$4^{th}$ Criterion:

Only the isoenergy layers that, according to the irradiation plan determined in the first pass, have the largest overall number of particles relative to the other isoenergy layers are determined and irradiated.

$5^{th}$ Criterion:

Only the isoenergy layers that, according to the first pass, make the largest dose contribution to the overall dose to be applied in the target value relative to the other isoenergy layers are determined and irradiated.

$6^{th}$ Criterion:

Only the isoenergy layers that, according to the first pass, make the largest contribution to a target function relative to the other isoenergy layers are determined and irradiated. The target function is used in determining the irradiation plan.

$7^{th}$ Criterion:

Only the isoenergy layers that, according to the first pass, have the largest dose compensation error relative to the other isoenergy layers are determined and irradiated. The dose compensation error specifies a measure for an error resulting from non-irradiation of an isoenergy layer despite corresponding compensation by irradiated isoenergy layers.

$8^{th}$ Criterion:

To determine the set of isoenergy layers to be irradiated, a set of isoenergy layers that are to be irradiated according to the irradiation plan of the first pass is assumed in accordance with the $8^{th}$ criterion. The set is used to start the optimization described below. The set may include no isoenergy layers or only a single isoenergy layer. A first target function value is determined based on an irradiation plan optimized or generated based on the set of isoenergy layers, such that correspondence between the actual dose and the intended dose is maximized. The isoenergy layer whose addition to the set, after optimization of a fictitious irradiation plan, leads to a second target function value having the greatest distance from the first target function value (e.g., the greatest improvement) is sought.

When the greatest distance in terms of magnitude is greater than a predetermined distance threshold, the corresponding isoenergy layer is added to the set, such that the first target function value corresponds to the second target function value. The procedure is repeated. The set of isoenergy layers to be irradiated is expanded until no further isoenergy layer is found whose addition to the set, after optimization of a fictitious irradiation plan, leads to a new second target function value having a distance from the new first target function value that is greater than the predetermined distance threshold.

In some embodiments, the above-described second method in accordance with the present teachings is an inversely operating variant of the above-described first method in accordance with the present teachings. The result (e.g., the set of irradiated isoenergy layers or the set of non-irradiated isoenergy layers) of the second method may substantially correspond to the result of the first method. While the first method starts with all isoenergy layers and subsequently excludes specific isoenergy layers from irradiation according to specific criteria, the second method determines the isoenergy layers to be irradiated based on corresponding criteria.

In the second method, as in the first method, a ratio may be formed between the numbers or proportions, in accordance with the respective criterion, of the specific isoenergy layers and a sum of the numbers or proportions, in accordance with the respective criterion, of all isoenergy layers. The specific isoenergy layers are selected such that the ratio lies just above a predetermined threshold but falls below the predetermined threshold upon the removal of just one of the specific isoenergy layers.

The specific isoenergy layers may be selected such that the sum of the numbers or proportions, in accordance with the respective criterion, of the specific isoenergy layers lies just above a predetermined maximum value but falls below the predetermined maximum value upon the removal of just one of the specific isoenergy layers.

A specific condition may be prescribed for the irradiation plan. An isoenergy layer is added to the specific isoenergy layers until, as a result of adding the last-added isoenergy layer, the irradiation plan determined thereby complies with the condition.

In some embodiments, the criterion or criteria used for determining the irradiation plan may depend on an angle range that is formed between two fields by which the target volume is irradiated. Moreover, the criterion or criteria used for determining the irradiation plan may further depend on the geometry of the target volume.

By way of example, the specific criteria may only be used when using opposing fields or when using two fields that form an angle of at least 120°. However, in accordance with the present teachings, work may be conducted with more than two fields during the irradiation.

As used herein, a "field" refers to irradiation from a specific direction. For an opposing field, irradiation is effected from two substantially opposing directions. For example, when using an opposing field, the isoenergy layers with the smallest or greatest energy may not be irradiated since the corresponding non-irradiated regions may be covered by the isoenergy layers with the greatest or smallest energy of the respective other field.

For a convex target volume that is embedded in a homogeneous region of an examination object (e.g., a patient), there are, for example, voxels in the target volume that are occupied by particles from both a particle beam operating at a high energy of a first field and a particle beam operating at a comparatively lower energy of a second different field.

In accordance with the present teachings, a first device and a further second device configured for determining an irradiation plan for a particle irradiation unit are provided. Depending on the determined irradiation plan, the particle irradiation unit is configured to irradiate a target volume in an examination object with a particle beam. Each of the first device and the second device includes an input part, a computing part, and an output part. The target volume and a predetermined dose distribution (e.g., intended dose distribution) are prescribed for the respective device by the input part. The computing part determines the irradiation plan in a first pass, such that the particles of the particle beam are delivered to the target volume in accordance with the predetermined dose distribution. The target volume includes a plurality of isoenergy layers. The irradiation plan is output by the output part.

The computing part of the first device in accordance with the present teachings determines the irradiation plan in a second pass with an additional condition that the device does not irradiate at least one of the isoenergy layers. The computing part determines the at least one isoenergy layer (e.g., the n isoenergy layers) according to at least one of the criteria described above in connection with the first method in accordance with the present teachings.

By contrast, the computing part of the second device in accordance with the present teachings determines the irradiation plan in a second pass with an additional condition that only specific isoenergy layers of the plurality of isoenergy layers are irradiated. The computing part determines the specific isoenergy layers according to at least one of the criteria described above in connection with the second method in accordance with the present teachings.

Advantages of the first device and the second device in accordance with the present teachings substantially correspond to advantages of the first method and second method in accordance with the present teachings that are explained in detail above.

In some embodiments, a particle irradiation unit with a device in accordance with the present teachings is provided.

In some embodiments, a computer program product (e.g., software) that is configured to be loaded into a memory of a programmable control apparatus or computing part of a particle irradiation unit is provided. Using the computer program product, one or more of the above-described embodiments of methods in accordance with the present teachings may be executed (e.g., when the computer program product runs in the control apparatus). The computer program product may use a program part (e.g., libraries and auxiliary functions) for realizing corresponding embodiments of a method in accordance with the present teachings. Thus, a computer program product may include software used to execute a method in accordance with the present teachings. The software may be a source code (e.g., C++) to be compiled and linked or only interpreted. Alternatively, the software may be executable software code that, for execution purposes, is to be loaded into the corresponding computing part or control apparatus.

In some embodiments, an electronically readable data medium (e.g., a DVD, magnetic tape, or USB stick) is provided on which electronically readable control information (e.g., software, as described above) is stored. If the control information (e.g., software) is read from the data medium and stored in the control part or a computing unit of a particle irradiation unit, all of the above-described embodiments of a method in accordance with the present teachings may be performed.

The selection of one or more criteria for determining the isoenergy layers not to be irradiated or for determining the isoenergy layers to be irradiated may be prescribed by a user (e.g., either interactively or by a configuration setting).

As a result of the targeted reduction in the isoenergy layers (first variant) or the targeted use of only the most important isoenergy layers (second variant), the overall irradiation duration may be significantly shortened, thereby resulting in greater patient comfort and increased efficacy of the particle irradiation unit. In accordance with the present teachings, no intervention in the beam application or in the accelerator itself may be needed since such intervention relates merely to a software modification. As a result of parameter selectability (e.g., criteria selection) and display of the effects on the quality of the irradiation plan, an optimal compromise between reduced overall irradiation duration and quality of the irradiation plan may be determined on a case-by-case basis.

In some embodiments, the present teachings may be applied for increasing patient throughput in particle radiotherapy. However, the present teachings are not restricted to this field of application but may be used instead wherever energy or a dose is applied in a target volume by particles.

BRIEF DESCRIPTION OF THE DRAWINGS

FIG. 2 shows a schematic depiction of an example of irradiation of a target volume by an exemplary particle irradiation unit.

FIG. 3 shows a flowchart of an exemplary first variant in accordance with the present teachings.

FIG. 4 shows a flowchart of an exemplary second variant in accordance with the present teachings.

DETAILED DESCRIPTION

Figure 1:
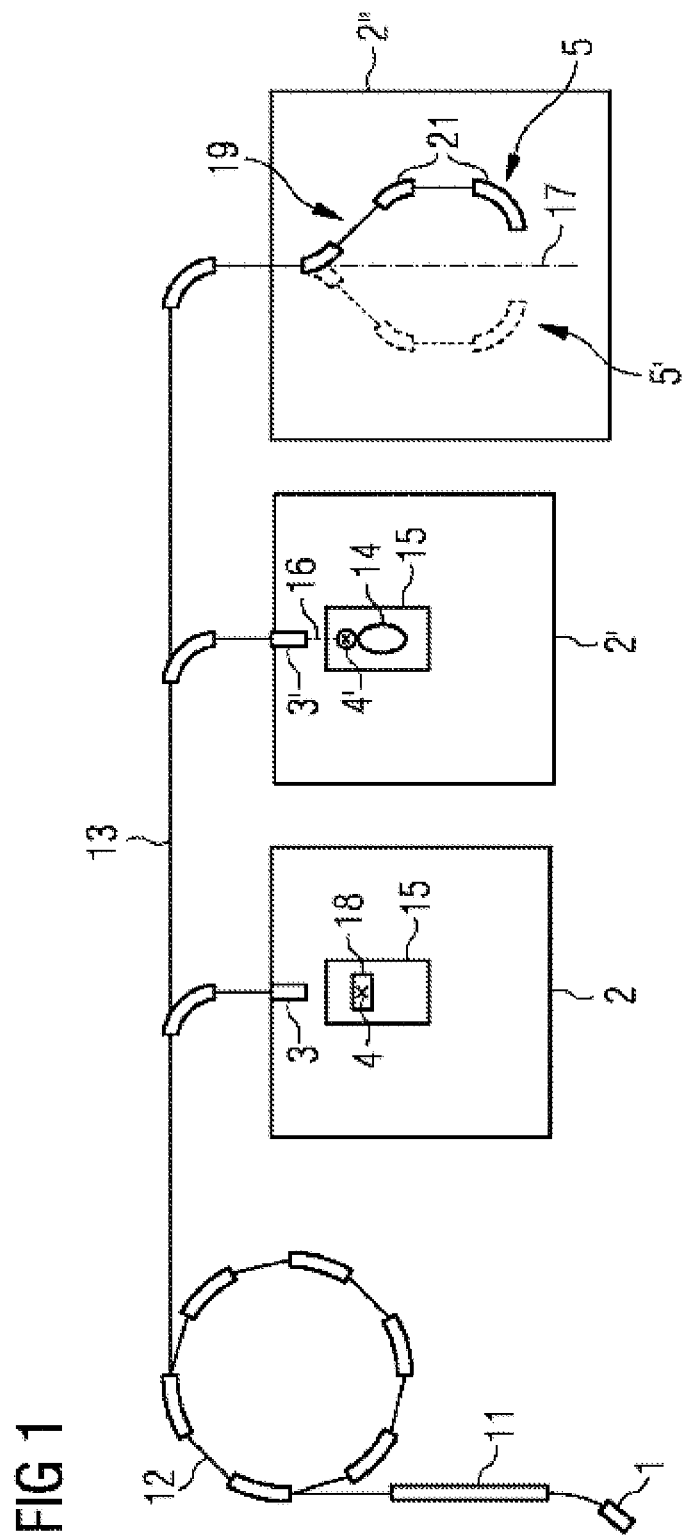
FIG. 1 shows a schematic depiction of an overview of an example of a particle irradiation unit.

The particle irradiation unit 20 shown in FIG. 1 irradiates a patient 14 in a second irradiation room 2'. The patient 14 is lying on a positioning device 15 (e.g., a table) and is irradiated with a beam that includes particles 16 (hereafter, to as a "particle beam 16"). By way of example, the particle beam 16 may be used to irradiate a tumor in the patient 14 using high-energy particles. However, the particle irradiation unit 20 may also be used to irradiate an inanimate object 18 (e.g., a water phantom), as is shown in a first irradiation room 2.

By way of example, protons, pions, helium ions, carbon ions, and ions from other elements may be used as particles. For example, the corresponding particles are generated in a particle source or ion source 1 and accelerated to a first energy level in a pre-accelerator 11 (e.g., a linear accelerator). The particles are accelerated to an energy for irradiation in a ring accelerator 12 (e.g., a synchrotron or cyclotron). The particle beam emerging from the ring accelerator 12 is transported by a high-energy beam transportation system 13 to one or more irradiation rooms (e.g., first irradiation room 2, second irradiation room 2', third irradiation room 2") and used therein for irradiating a target volume in a patient 14. The irradiation is effected from a fixed direction. Thus, the patient 14 or inanimate object 18 to be irradiated is arranged in advance in a spatially fixed manner by the positioning device 15 in the first irradiation room 2 and second irradiation room 2'. The first irradiation room 2 and the second irradiation room 2' are referred to as "fixed beam" rooms. By contrast, there is a gantry 19 in the third irradiation room 2". The gantry 19 is movable about an axis 17 (e.g., rotatably). The body to be irradiated may be irradiated from different directions (e.g., with different fields) by the gantry 19. For example, the particle beam 16 may be directed to the body to be irradiated with the aid of a beam guide 21 in the gantry 19. FIG. 1 depicts a first position 5 and a second position 5', although a plurality of positions may be implemented.

In the first irradiation room 2 and the second irradiation room 2', the particle beam 16 emerges from a first beam outlet 3 and second beam outlet 3' and impacts on the body 14 and the inanimate object 18, respectively, containing the target volume to be irradiated. The target volume may lie in the first isocenter 4 and the second isocenter 4' of the first irradiation room 2 and second irradiation room 2', respectively.

FIG. 2 shows a target volume 6 that is irradiated by a particle beam 16 generated by a particle irradiation unit 20. In addition to an irradiation-planning device 10, the particle irradiation unit 20 includes a beam generation device 30, a raster scan apparatus 23, and a controller 22 for the raster scan apparatus 23. The raster scan apparatus 23 includes a first particle deflection 24 and a second particle deflection 25. The first particle deflection 24 and the second particle deflection 25 may each include magnets. With the aid of the first particle deflection 24 and the second particle deflection 25, the particle beam 16 may be deflected both horizontally and vertically (e.g., as shown by the mutually perpendicular arrows x, y). The raster scan apparatus 23 may direct the particle beam 16 to any point $(x_i, y_i)$ on a surface in the x,y-plane. Each point, together with the respectively inserted particle energy, is referred to as a scan spot, raster point, or scan point. Thus, a raster point is determined, firstly, by the alignment of the particle beam 16 (x- or y-direction) and, secondly, by the particle energy thereof. In other words, there is a plurality of raster points with different particle energies for specific x- and y-coordinates. Taking into account the irradiated body that, for example, is established by a CT recording, the particle energy determines the coordinate in the z-direction (e.g., perpendicular to the x- and y-axes), wherein the z-position of the Bragg peak lies ever further in the direction of the particle beam 16 in the target volume 6 as the particle energy increases. However, since the penetration depth is dependent on the tissue or material through which the particle beam 16 passes, the above-described relationship only applies to the same x- and y-positions.

As used herein, the "Bragg peak" refers to the point or region at which the particle beam applies the greatest portion of its dose along the trajectory thereof.

The target volume 6 to be irradiated by the particle beam 16 may be irradiated in the form of isoenergy layers 7-9. Particles with the same energy are applied, respectively, in the raster points of the same isoenergy layer 7-9. Assuming that the particle beam 16 passes through a homogeneous volume on its path to the corresponding isoenergy layer 7-9, the isoenergy layers 7-9 lie perpendicular to the z-axis, as shown in simplified manner in FIG. 2.

To set the particle beam 16 to a corresponding isoenergy layer 7-9 (e.g., to position the Bragg peak on an isoenergy layer 7-9), the particles of the particle beam 16 are assigned an initial energy by the particles being accelerated to a velocity corresponding to the initial energy. The initial energy describes the energy of a particle that the particle has prior to impact on the body 14 or the inanimate object 18. To irradiate the isoenergy layer 7 closest to the first beam outlet 3 and second beam outlet 3' (e.g., furthest to the left in FIG. 2), the particles with the lowest energy may be used. To irradiate the isoenergy layer 9 that is furthest from the first beam outlet 3 and the second beam outlet 3' (e.g., furthest to the right in FIG. 2), the particles with the highest energy may be used.

To irradiate the whole target volume 6, the isoenergy layers 7-9 are irradiated in succession. Irradiation may be started at the isoenergy layer 9 that is furthest from the first beam outlet 3 and the second beam outlet 3'. The process may be continued with the respective adjacent isoenergy layer. To irradiate specific raster points in the same isoenergy layer 7-9 with different amounts of energy, the period of time during which the respective raster point is irradiated by the particle beam 16 may be varied. As the duration of irradiation by the particle beam 16 for the corresponding raster point increases, more energy (e.g., a higher dose) is deposited in the corresponding raster point.

In the target volume 6 shown in FIG. 2, the isoenergy layer 8 is being irradiated by the particle beam 16, while the three isoenergy layers 9 have already been irradiated and the four isoenergy layers 7 lying further to the left still await irradiation.

Before the target volume 6 is irradiated, an irradiation plan is generated. The irradiation plan effects the scanning of the target volume 6 by the particle beam 16. The irradiation plan may determine the control parameters for controlling the particle irradiation unit 20. The irradiation plan is generated using an irradiation-planning device 10 (e.g., a PC).

To perform the actual irradiation, the irradiation plan is forwarded from the irradiation-planning device 10 to the beam generation device 30 and the controller 22 of the raster scan apparatus 23. In FIG. 2, the irradiation-planning device 10 is shown as a component of the particle irradiation unit 20. In some embodiments, the irradiation plan generated by the irradiation-planning device 10 may be loaded onto a data medium 29. The irradiation plan may be loaded into the particle irradiation unit 20 from the data medium 29. The irradiation-planning device 10 and the particle irradiation unit 20 may not be linked by a communication-technical part. Time (e.g., days) may elapse between generating the irradiation plan and performing the irradiation based on the irradiation plan.

To generate the irradiation plan, the irradiation-planning device 10 uses the location and dimensions of the target volume 6 to be irradiated (e.g., a tumor to be irradiated). A knowledge of the nature of the tissue that the particle beam 16 passes through on the way to the target volume 6 may be used when irradiating a patient 14. By way of example, the information may be established by a computed tomography or magnetic resonance imaging scanner, and transmitted to the irradiation-planning device 10 by an input part 26. Starting from this information and a predetermined dose distribution (e.g., intended dose distribution), the irradiation-planning device 10 determines the irradiation plan with the aid of the computing part 27 thereof. The irradiation plan may specify how many particles with a specific energy are to be applied at a raster point.

Ideally, a patient may be fixed during irradiation to minimize movement of the target volume 6. For this reason, the irradiation duration may be minimized. Moreover, a short irradiation duration facilitates a higher patient throughput. Correspondence between the dose distribution in accordance with the irradiation plan and the intended dose distribution may be maximized. Since the number of irradiated isoenergy layers in accordance with the present teachings is smaller than in the conventional approach, an irradiation plan generated in accordance with the present teachings has a shorter overall irradiation duration.

FIG. 3 shows a flowchart of an exemplary first variant of the present teachings.

In a first act S1, a target volume, an intended dose distribution, a plan quality to be complied with of the irradiation plan to be generated, and a criterion for selecting isoenergy layers are prescribed to generate an irradiation plan.

The plan quality may include the quality of the dose distribution (e.g., the quality with which the dose of the particle beam is applied based on the irradiation plan). By way of example, the quality of the dose distribution may be determined based on observations of specific tolerance limits of organs at risk, dose/volume histograms, observations of tolerance limits with respect to the dose distribution in the target volume (e.g., "dose constraints of planning target volume"), and/or the correspondence between the actual dose distribution and the intended dose distribution. For example, the absolute values of the actual dose distribution (e.g., in accordance with the irradiation plan) correspond to the absolute values of the intended dose distribution.

In a second act S2, the isoenergy layers that initially define the set of isoenergy layers are determined dependent on the prescribed target volume.

In a third act S3, the preliminary irradiation plan is generated based on the prescribed intended dose distribution and the set of isoenergy layers. The irradiation plan inter alia sets the number of raster points included by each isoenergy layer in the set, and the number of particles with which each one of the raster points is to be irradiated (e.g., in order to reach the intended dose distribution as a result of the irradiation and other boundary conditions). The irradiation plan also sets the overall number of particles for each isoenergy layer in the set.

A check is carried out in the fourth act S4 as to whether the irradiation plan generated in act S3 complies with the prescribed plan quality.

If the irradiation plan generated in act S3 complies with the prescribed plan quality, an isoenergy layer is removed from the set depending on the predetermined criterion in the fifth act S5. By way of example, the criterion may be the raster-point number or the overall number of particles, such that the isoenergy layer that, according to the current irradiation plan, has the smallest raster-point number or the smallest overall number of particles is removed from the set.

The method branches back to act S3, wherein a new irradiation plan is generated again based on the now reduced set of isoenergy layers. Acts S3 through S5 are carried out until the irradiation plan no longer complies with the prescribed plan quality. In some cases, the current irradiation plan may be used as the final irradiation plan for performing the irradiation. In other cases, the last-removed isoenergy layer may be returned to the set of isoenergy layers and an irradiation plan may be generated based on the set and used for irradiation. In some embodiments, the irradiation plan may also be determined prior to the current irradiation plan and stored, such that the stored irradiation plan may immediately be used as the final irradiation plan if the current or last-determined irradiation plan does not comply with the plan quality.

FIG. 4 shows a flowchart of an exemplary second variant of the present teachings.

The flowchart of the second variant has similarities to the flowchart of the first variant. In accordance with the first variant, isoenergy layers are removed from the set of isoenergy layers according to specific criteria until the plan quality is only just still acceptable. By contrast, in accordance with the second variant, isoenergy layers are added to the set according to specific criteria until the plan quality is acceptable.

In the second variant, a target volume, an intended dose distribution, a plan quality to be complied with, and a criterion are also predetermined in a first act S1.

As in the first variant, the isoenergy layers in the second variant are determined depending on the target volume in the second act S2. The isoenergy layers are determined as in the first variant such that pervasion of the target volume by the isoenergy layers is maximized.

In the third act S3, an irradiation plan is determined based on the isoenergy layers thus determined.

In the fourth act S14, a set of isoenergy layers is determined. When determining the set of isoenergy layers, the predetermined criterion may be used. For example, the isoenergy layers having the most raster points or having the largest overall number of particles (in accordance with the irradiation plan generated in act S3) are selected. However, an empty set may also be determined in act S14. Alternatively, only one isoenergy layer may be determined as the set (e.g., the isoenergy layer that appears to have the best compliance with the predetermined criterion).

An irradiation plan is determined in act S15 based on the specific set of isoenergy layers. The plan quality of the irradiation plan is checked in act S16. In act S17, if the plan quality of the irradiation plan is not satisfied (as may often be the case during the first pass), an isoenergy layer not yet present in the set is added to the set based on the predetermined criterion. By way of example, from the isoenergy layers not yet contained in the set, the isoenergy layer having the most raster points or the largest overall number of particles in accordance with the irradiation plan generated in act S3 may be added. The flowchart of the second variant branches back to act S15, wherein a better irradiation plan is determined based on the expanded set of isoenergy layers.

The method ends in act S16 upon a determination that the set of isoenergy layers is sufficient, and that the irradiation plan generated therewith complies with the predetermined plan quality. At this stage, the current irradiation plan corresponds to the final irradiation plan with which the irradiation is performed.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A method for determining an irradiation plan for a particle irradiation unit, the particle irradiation unit being configured to irradiate a target volume in an examination object with a particle beam based on the irradiation plan, the method comprising:
   prescribing the target volume and a predetermined dose distribution;
   determining the irradiation plan in a first pass to apply the particle beam based on the predetermined dose distribution in the target volume, the target volume comprising a plurality of isoenergy layers;
   determining the irradiation plan in a second pass with an additional condition that at least one isoenergy layer of the plurality of isoenergy layers is not irradiated; and
   determining the at least one isoenergy layer of the plurality of isoenergy layers based on a criterion selected from the group consisting of:
   (a) the at least one isoenergy layer is not irradiated if the particle beam has an energy below a minimum peak energy;
   (b) the at least one isoenergy layer is not irradiated if the particle beam has an energy above a maximum peak energy;
   (c) the at least one isoenergy layer is not irradiated if, according to the irradiation plan determined in the first pass, the at least one isoenergy layer has a smallest number of raster points;
   (d) the at least one isoenergy layer is not irradiated if, according to the irradiation plan determined in the first pass, the at least one isoenergy layer has a smallest overall number of particles;
   (e) the at least one isoenergy layer is not irradiated if, according to the irradiation plan determined in the first pass, the at least one isoenergy layer makes a smallest dose contribution to an overall dose to be applied in the target volume;
   (f) the at least one isoenergy layer is not irradiated if, according to the irradiation plan determined in the first pass, the at least one isoenergy layer makes a smallest contribution to a target function, the target function being calculated for determining the irradiation plan;
   (g) the at least one isoenergy layer is not irradiated if, according to the irradiation plan determined in the first pass, the at least one isoenergy layer has a smallest dose compensation error, wherein the dose compensation error defines an error resulting from non-irradiation of the at least one isoenergy layer despite corresponding compensation by irradiated isoenergy layers;
   (h) the at least one isoenergy layer is not irradiated if the at least one isoenergy layer has a first target function value having a smallest change in relation to a second target function value, wherein the first target function value is determined based on an irradiation plan generated under an assumption that the at least one isoenergy layer is not irradiated, and wherein the second target function value is generated based on the irradiation plan determined in the first pass; and
   (i) combinations thereof.

2. The method of claim 1, further comprising:
forming a ratio between a number or a proportion of the at least one isoenergy layer and a sum of numbers or proportions of all isoenergy layers of the plurality of isoenergy layers;
   wherein the at least one isoenergy layer is selected such that the ratio lies below a predetermined threshold but will exceed the predetermined threshold if an additional isoenergy layer of the plurality of isoenergy layers is added to the at least one isoenergy layer.

3. The method of claim 1, further comprising:
forming a sum of a number or a proportion of the at least one isoenergy layer;
selecting the at least one isoenergy layer such that the sum lies below a predetermined maximum value but will exceed the predetermined maximum value if an additional isoenergy layer of the plurality of isoenergy layers is added to the at least one isoenergy layer.

4. The method of claim 1, further comprising:
prescribing a condition to be complied with by the irradiation plan; and
adding additional isoenergy layers to the at least one isoenergy layer until the irradiation plan does not comply with the condition.

5. The method claim 1, further comprising:
determining a set of isoenergy layers, wherein the set comprises each isoenergy layer of the plurality of isoenergy layers except for the at least one isoenergy layer;
re-performing the first pass for determining the irradiation plan starting from the set of isoenergy layers; and
determining the irradiation plan in the second pass with additional conditions that at least one isoenergy layer of the set of isoenergy layers is not irradiated, and that at least one isoenergy layer of the set of isoenergy layers is determined according to at least one of the criteria.

6. A method for determining an irradiation plan for a particle irradiation unit, the particle irradiation unit being configured to irradiate a target volume in an examination object with a particle beam based on the irradiation plan, the method comprising:
prescribing the target volume and a predetermined dose distribution;
determining the irradiation plan in a first pass to apply the particle beam based on the predetermined dose distribution in the target volume, the target volume comprising a plurality of isoenergy layers;
determining the irradiation plan in a second pass with an additional condition that only specific isoenergy layers of the plurality of isoenergy layers are irradiated; and
determining the specific isoenergy layers of the plurality of isoenergy layers based on a criterion selected from the group consisting of:
(a) only the specific isoenergy layers are irradiated if the particle beam has an energy above a minimum peak energy;
(b) only the specific isoenergy layers are irradiated if the particle beam has an energy below a maximum peak energy;
(c) only the specific isoenergy layers are irradiated if, according to the irradiation plan determined in the first pass, the specific isoenergy layers have a largest number of raster points;
(d) only the specific isoenergy layers are irradiated if, according to the irradiation plan determined in the first pass, the specific isoenergy layers have a largest overall number of particles;
(e) only the specific isoenergy layers are irradiated if, according to the irradiation plan determined in the first pass, the specific isoenergy layers make a largest dose contribution to an overall dose to be applied in the target volume;
(f) only the specific isoenergy layers are irradiated if, according to the irradiation plan determined in the first pass, the specific isoenergy layers make a largest contribution to a target function, the target function being calculated for determining the irradiation plan;
(g) only the specific isoenergy layers are irradiated if, according to the irradiation plan determined in the first pass, the specific isoenergy layers have a largest dose compensation error, wherein the dose compensation error defines an error resulting from non-irradiation of the specific isoenergy layers despite corresponding compensation by irradiated isoenergy layers;
(h) the specific isoenergy layers are determined from a set of isoenergy layers based on the irradiation plan determined in the first pass, wherein a first target function value is generated based on an irradiation plan generated under an assumption that only the set of isoenergy layers is irradiated, wherein in each case an isoenergy layer is added to the set of isoenergy layers that modifies a second target function value in relation to the first target function value to a greatest extent, wherein the second target function value is determined based on an irradiation plan generated under an assumption that only the added isoenergy layer and the set of isoenergy layers are irradiated, wherein an additional isoenergy layer is added to the set of isoenergy layers if a change of the second target function value in relation to the first target function value is greater than a predetermined distance threshold; and
(i) combinations thereof.

7. The method of claim 6, further comprising:
forming a ratio between numbers or proportions of the specific isoenergy layers and a sum of numbers or proportions of all isoenergy layers of the plurality of isoenergy layers;
wherein the specific isoenergy layers are selected such that the ratio lies above a predetermined threshold but will fall below the predetermined threshold if a number of the specific isoenergy layers is reduced by one.

8. The method of claim 6, further comprising:
forming a sum of numbers or proportions of the specific isoenergy layers;
selecting the specific isoenergy layers such that the sum lies above a predetermined maximum value but will fall below the predetermined maximum value if a number of the specific isoenergy layers is reduced by one.

9. The method of claim 6, further comprising:
prescribing a condition to be complied with by the irradiation plan; and
adding at least one isoenergy layer to the specific isoenergy layers in accordance with the criterion until the irradiation plan complies with the condition.

10. The method of claim 1, wherein the criterion depends on an angle range formed between two fields for irradiating the target volume a geometry of the target volume, or a combination of the angle range and the geometry.

11. The method of claim 1, wherein the target function comprises a penalty term, and wherein the penalty term increases with increasing number of irradiated isoenergy layers.

12. A device configured for determining an irradiation plan for a particle irradiation unit, the particle irradiation unit being configured to irradiate a target volume in an examination object with a particle beam based on the irradiation plan, wherein the device comprises:
an input part;
a computing part; and
an output part;
wherein the input part is configured to prescribe the target volume and a predetermined dose distribution for the device;
wherein the computing part is configured to determine the irradiation plan in a first pass to apply the particle beam in the target volume based on the predetermined dose distribution, the target volume comprising a plurality of isoenergy layers;
wherein the output part is configured to output the irradiation plan;
wherein the input part is further configured to prescribe at least one criterion for the plurality of isoenergy layers for the device;
wherein the computing part is further configured to determine the irradiation plan in a second pass with an additional condition that at least one isoenergy layer of the plurality of isoenergy layers is not irradiated; and wherein the computing part is further configured to determine the at least one isoenergy layer of the plurality of isoenergy layers that is not to be irradiated based on at least one criterion; and wherein the at least one criterion is selected from the group consisting of:
- (a) the device does not irradiate the at least one isoenergy layer if the particle beam has an energy below a minimum peak energy;
- (b) the device does not irradiate the at least one isoenergy layer if the particle beam has an energy above a maximum peak energy;
- (c) the device does not irradiate the at least one isoenergy layer if, according to the irradiation plan determined in the first pass, the at least one isoenergy layer has a smallest number of raster points;
- (d) the device does not irradiate the at least one isoenergy layer if, according to the irradiation plan determined in the first pass, the at least one isoenergy layer has a smallest overall number of particles;
- (e) the device does not irradiate the at least one isoenergy layer if, according to the irradiation plan determined in the first pass, the at least one isoenergy layer makes a smallest dose contribution to an overall dose to be applied in the target volume;
- (f) the device does not irradiate the at least one isoenergy layer if, according to the irradiation plan determined in the first pass, the at least one isoenergy layer makes a smallest contribution to a target function, the target function being calculated for determining the irradiation plan;
- (g) the device does not irradiate the at least one isoenergy layer if, according to the irradiation plan determined in the first pass, the at least one isoenergy layer has a smallest dose compensation error, wherein the dose compensation error defines an error resulting from non-irradiation of the at least one isoenergy layer despite corresponding compensation by irradiated isoenergy layers;
- (h) the device does not irradiate the at least one isoenergy layer if the at least one isoenergy layer has a first target function value having a smallest change in relation to a second target function value, wherein the first target function value is determined based on an irradiation plan generated under an assumption that the at least one isoenergy layer is not irradiated, and wherein a second target function value is generated based on the irradiation plan determined in the first pass; and
- (i) combinations thereof.

13. A device configured for determining an irradiation plan for a particle irradiation unit, the particle irradiation unit being configured to irradiate a target volume in an examination object with a particle beam based on the irradiation plan, wherein the device comprises:

an input part;
a computing part; and
an output part;

wherein the input part is configured to prescribe the target volume and a predetermined dose distribution for the device;

wherein the computing part is configured to determine the irradiation plan in a first pass to apply the particle beam in the target volume based on the predetermined dose distribution, the target volume comprising a plurality of isoenergy layers;

wherein the output part is configured to output the irradiation plan;

wherein the input part is further configured to prescribe at least one criterion for the isoenergy layers for the device;

wherein the computing part is further configured to determine the irradiation plan in a second pass with an additional condition that only specific isoenergy layers of the plurality of isoenergy layers are irradiated;

wherein the computing part is further configured to determine the specific isoenergy layers of the plurality of isoenergy layers based on at least one criterion; and wherein the at least one criterion is selected from the group consisting of:
- (a) the device only irradiates the specific isoenergy layers if the particle beam has an energy above a minimum peak energy;
- (b) the device only irradiates the specific isoenergy layers if the particle beam has an energy below a maximum peak energy;
- (c) the device only irradiates the specific isoenergy layers if, according to the irradiation plan determined in the first pass, the specific isoenergy layers have a largest number of raster points;
- (d) the device only irradiates the specific isoenergy layers if, according to the irradiation plan determined in the first pass, the specific isoenergy layers have a largest overall number of particles;
- (e) the device only irradiates the specific isoenergy layers if, according to the irradiation plan determined in the first pass, the specific isoenergy layers make a largest dose contribution to an overall dose to be applied in the target volume;
- (f) the device only irradiates the specific isoenergy layers if, according to the irradiation plan determined in the first pass, the specific isoenergy layers make a largest contribution to a target function, the target function being calculated for determining the irradiation plan;
- (g) the device only irradiates the specific isoenergy layers if, according to the irradiation plan determined in the first pass, the specific isoenergy layers have a largest dose compensation error, wherein the dose compensation error defines an error resulting from non-irradiation of the specific isoenergy layers despite corresponding compensation by irradiated isoenergy layers;
- (h) the device only irradiates the specific isoenergy layers determined from a set of isoenergy layers based on the irradiation plan determined in the first pass, wherein a first target function value is generated based on an irradiation plan generated under an assumption that only the set of isoenergy layers is irradiated, wherein in each case an isoenergy layer is added to the set of isoenergy layers that modifies a second target function value in relation to the first target function value to a greatest extent, wherein the second target function value is determined based on an irradiation plan generated under an assumption that only the added isoenergy layer and the set of isoenergy layers are irradiated, wherein an additional isoenergy layer is added to the set of isoenergy layers if a change of the second target function value in relation to the first target function value is greater than a predetermined distance threshold; and
(i) combinations thereof.

14. A method for determining an irradiation plan for a particle irradiation unit, the particle irradiation unit being configured to irradiate a target volume in an examination object with a particle beam based on the irradiation plan, the method comprising:
    providing a device configured for determining the irradiation plan, the device comprising an input part, a computing part, and an output part;
    prescribing, using the input part, the target volume and a predetermined dose distribution;
    determining, using the computing part, the irradiation plan in a first pass to apply the particle beam based on the predetermined dose distribution in the target volume, the target volume comprising a plurality of isoenergy layers;
    determining, using the computing part, the irradiation plan in a second pass with an additional condition that at least one isoenergy layer of the plurality of isoenergy layers is not irradiated; and
    determining, using the computing part, the at least one isoenergy layer of the plurality of isoenergy layers based on a criterion selected from the group consisting of:
        (a) the at least one isoenergy layer is not irradiated if the particle beam has an energy below a minimum peak energy;
        (b) the at least one isoenergy layer is not irradiated if the particle beam has an energy above a maximum peak energy;
        (c) the at least one isoenergy layer is not irradiated if, according to the irradiation plan determined in the first pass, the at least one isoenergy layer has a smallest number of raster points;
        (d) the at least one isoenergy layer is not irradiated if, according to the irradiation plan determined in the first pass, the at least one isoenergy layer has a smallest overall number of particles;
        (e) the at least one isoenergy layer is not irradiated if, according to the irradiation plan determined in the first pass, the at least one isoenergy layer makes a smallest dose contribution to an overall dose to be applied in the target volume;
        (f) the at least one isoenergy layer is not irradiated if, according to the irradiation plan determined in the first pass, the at least one isoenergy layer makes a smallest contribution to a target function, the target function being calculated for determining the irradiation plan;
        (g) the at least one isoenergy layer is not irradiated if, according to the irradiation plan determined in the first pass, the at least one isoenergy layer has a smallest dose compensation error, wherein the dose compensation error defines an error resulting from non-irradiation of the at least one isoenergy layer despite corresponding compensation by irradiated isoenergy layers;
        (h) the at least one isoenergy layer is not irradiated if the at least one isoenergy layer has a first target function value having a smallest change in relation to a second target function value, wherein the first target function value is determined based on an irradiation plan generated under an assumption that the at least one isoenergy layer is not irradiated, and wherein the second target function value is generated based on the irradiation plan determined in the first pass; and
        (i) combinations thereof.

15. A particle irradiation unit comprising a device configured for determining an irradiation plan for the particle irradiation unit, the particle irradiation unit being configured to irradiate a target volume in an examination object with a particle beam based on the irradiation plan, wherein the device comprises:
    an input part;
    a computing part; and
    an output part;
        wherein the input part is configured to prescribe the target volume and a predetermined dose distribution for the device;
        wherein the computing part is configured to determine the irradiation plan in a first pass to apply the particle beam in the target volume based on the predetermined dose distribution, the target volume comprising a plurality of isoenergy layers;
        wherein the output part is configured to output the irradiation plan;
        wherein the input part is further configured to prescribe at least one criterion for the isoenergy layers for the device;
        wherein the computing part is further configured to determine the irradiation plan in a second pass with an additional condition that at least one isoenergy layer of the plurality of isoenergy layers is not irradiated; and
        wherein the computing part is further configured to determine the at least one isoenergy layer of the plurality of isoenergy layers that is not to be irradiated based on at least one criterion; and
        wherein the at least one criterion is selected from the group consisting of:
            (a) the device does not irradiate the at least one isoenergy layer if the particle beam has an energy below a minimum peak energy;
            (b) the device does not irradiate the at least one isoenergy layer if the particle beam has an energy above a maximum peak energy;
            (c) the device does not irradiate the at least one isoenergy layer if, according to the irradiation plan determined in the first pass, the at least one isoenergy layer has a smallest number of raster points;
            (d) the device does not irradiate the at least one isoenergy layer if, according to the irradiation plan determined in the first pass, the at least one isoenergy layer has a smallest overall number of particles;
            (e) the device does not irradiate the at least one isoenergy layer if, according to the irradiation plan determined in the first pass, the at least one isoenergy layer makes a smallest dose contribution to an overall dose to be applied in the target volume;
            (f) the device does not irradiate the at least one isoenergy layer if, according to the irradiation plan determined in the first pass, the at least one isoenergy layer makes a smallest contribution to a target function, the target function being calculated for determining the irradiation plan;
            (g) the device does not irradiate the at least one isoenergy layer if, according to the irradiation plan determined in the first pass, the at least one isoenergy layer has a smallest dose compensation error, wherein the dose compensation error defines an error resulting from non-irradiation of the at least one isoenergy layer despite corresponding compensation by irradiated isoenergy layers;
            (h) the device does not irradiate the at least one isoenergy layer if the at least one isoenergy layer has a first target function value having a smallest change in relation to a second target function value, wherein the first target function value is determined based on an irradiation plan generated under an assumption that the at least one isoenergy layer is not irradiated and wherein a second target function value is generated based on the irradiation plan determined in the first pass; and (i) combinations thereof.

16. A computer program product comprising a program, the computer program product being directly loadable into a memory of a programmable control apparatus of a particle irradiation unit, the program comprising instructions executable by a programmed processor for determining an irradiation plan for the particle irradiation unit, the particle irradiation unit being configured to irradiate a target volume in an examination object with a particle beam based on the irradiation plan, the method comprising:

prescribing the target volume and a predetermined dose distribution;

determining the irradiation plan in a first pass to apply the particle beam based on the predetermined dose distribution in the target volume, the target volume comprising a plurality of isoenergy layers;

determining the irradiation plan in a second pass with an additional condition that at least one isoenergy layer of the plurality of isoenergy layers is not irradiated; and determining the at least one isoenergy layer of the plurality of isoenergy layers based on a criterion selected from the group consisting of:

(a) the at least one isoenergy layer is not irradiated if the particle beam has an energy below a minimum peak energy;

(b) the at least one isoenergy layer is not irradiated if the particle beam has an energy above a maximum peak energy;

(c) the at least one isoenergy layer is not irradiated if, according to the irradiation plan determined in the first pass, the at least one isoenergy layer has a smallest number of raster points;

(d) the at least one isoenergy layer is not irradiated if, according to the irradiation plan determined in the first pass, the at least one isoenergy layer has a smallest overall number of particles;

(e) the at least one isoenergy layer is not irradiated if, according to the irradiation plan determined in the first pass, the at least one isoenergy layer makes a smallest dose contribution to an overall dose to be applied in the target volume;

(f) the at least one isoenergy layer is not irradiated if, according to the irradiation plan determined in the first pass, the at least one isoenergy layer makes a smallest contribution to a target function, the target function being calculated for determining the irradiation plan;

(g) the at least one isoenergy layer is not irradiated if, according to the irradiation plan determined in the first pass, the at least one isoenergy layer has a smallest dose compensation error, wherein the dose compensation error defines an error resulting from non-irradiation of the at least one isoenergy layer despite corresponding compensation by irradiated isoenergy layers;

(h) the at least one isoenergy layer is not irradiated if the at least one isoenergy layer has a first target function value having a smallest change in relation to a second target function value, wherein the first target function value is determined based on an irradiation plan generated under an assumption that the at least one isoenergy layer is not irradiated, and wherein the second target function value is generated based on the irradiation plan determined in the first pass; and (i) combinations thereof.

17. A non-transitory computer-readable storage medium having electronically readable control information stored therein, the electronically-readable control information representing instructions executable by a programmed processor for determining an irradiation plan for the particle irradiation unit, the particle irradiation unit being configured to irradiate a target volume in an examination object with a particle beam based on the irradiation plan, the method comprising:

prescribing the target volume and a predetermined dose distribution;

determining the irradiation plan in a first pass to apply the particle beam based on the predetermined dose distribution in the target volume, the target volume comprising a plurality of isoenergy layers;

determining the irradiation plan in a second pass with an additional condition that at least one isoenergy layer of the plurality of isoenergy layers is not irradiated; and determining the at least one isoenergy layer of the plurality of isoenergy layers based on a criterion selected from the group consisting of:

(a) the at least one isoenergy layer is not irradiated if the particle beam has an energy below a minimum peak energy;

(b) the at least one isoenergy layer is not irradiated if the particle beam has an energy above a maximum peak energy;

(c) the at least one isoenergy layer is not irradiated if, according to the irradiation plan determined in the first pass, the at least one isoenergy layer has a smallest number of raster points;

(d) the at least one isoenergy layer is not irradiated if, according to the irradiation plan determined in the first pass, the at least one isoenergy layer has a smallest overall number of particles;

(e) the at least one isoenergy layer is not irradiated if, according to the irradiation plan determined in the first pass, the at least one isoenergy layer makes a smallest dose contribution to an overall dose to be applied in the target volume;

(f) the at least one isoenergy layer is not irradiated if, according to the irradiation plan determined in the first pass, the at least one isoenergy layer makes a smallest contribution to a target function, the target function being calculated for determining the irradiation plan;

(g) the at least one isoenergy layer is not irradiated if, according to the irradiation plan determined in the first pass, the at least one isoenergy layer has a smallest dose compensation error, wherein the dose compensation error defines an error resulting from non-irradiation of the at least one isoenergy layer despite corresponding compensation by irradiated isoenergy layers;

(h) the at least one isoenergy layer is not irradiated if the at least one isoenergy layer has a first target function value having a smallest change in relation to a second target function value, wherein the first target function value is determined based on an irradiation plan generated under an assumption that the at least one isoenergy layer is not irradiated, and wherein the second target function value is generated based on the irradiation plan determined in the first pass; and (i) combinations thereof.

18. The method claim 2, further comprising:
prescribing a condition to be complied with by the irradiation plan; and
adding additional isoenergy layers to the at least one isoenergy layer until the irradiation plan does not comply with the condition.

19. The method claim 3, further comprising:
prescribing a condition to be complied with by the irradiation plan; and
adding additional isoenergy layers to the at least one isoenergy layer until the irradiation plan does not comply with the condition.

20. The method of claim 2, further comprising:
determining a set of isoenergy layers, wherein the set comprises each isoenergy layer of the plurality of isoenergy layers except for the at least one isoenergy layer;
re-performing the first pass for determining the irradiation plan starting from the set of isoenergy layers;
determining the irradiation plan in the second pass with additional conditions that at least one isoenergy layer of the set of isoenergy layers is not irradiated, and that at least one isoenergy layer of the set of isoenergy layers is determined according to at least one of the criteria.

* * * * *